(12) United States Patent  (10) Patent No.: US 8,523,877 B2
Ichinohe et al.  (45) Date of Patent: Sep. 3, 2013

(54) INTRAOCULAR LENS INSERTING INSTRUMENT

(75) Inventors: Takashi Ichinohe, Saitama (JP); Kazunori Kudoh, Saitama (JP)

(73) Assignee: Hoya Corporation, Tokyo (JP)

( * ) Notice: Subject to any disclaimer, the term of this patent is extended or adjusted under 35 U.S.C. 154(b) by 337 days.

(21) Appl. No.: 11/816,676

(22) PCT Filed: Jan. 12, 2006

(86) PCT No.: PCT/JP2006/300291
§ 371 (c)(1), (2), (4) Date: Aug. 20, 2007

(87) PCT Pub. No.: WO2006/090531
PCT Pub. Date: Aug. 31, 2006

(65) Prior Publication Data
US 2009/0204122 A1 Aug. 13, 2009

(30) Foreign Application Priority Data
Feb. 24, 2005 (JP) .................................. 2005-049700

(51) Int. Cl.
A61F 9/00 (2006.01)

(52) U.S. Cl.
USPC ........................................................ 606/107

(58) Field of Classification Search
USPC ........ 606/107, 108, 166; 623/6.12; 600/107, 600/108, 166
See application file for complete search history.

(56) References Cited

U.S. PATENT DOCUMENTS

| | | | |
|---|---|---|---|
| 2,761,446 A | 9/1956 | Reed | |
| 4,205,747 A | 6/1980 | Gilliam et al. | |
| 4,269,307 A | 5/1981 | LaHaye | |
| 4,423,809 A | 1/1984 | Mazzocco | |
| 4,573,998 A | 3/1986 | Mazzocco | |
| 4,608,049 A | 8/1986 | Kelman | |
| 4,634,423 A | 1/1987 | Bailey | |
| 4,681,102 A | 7/1987 | Bartell | |
| 4,697,697 A | 10/1987 | Graham et al. | |
| 4,699,140 A | 10/1987 | Holmes | |
| 4,702,244 A | 10/1987 | Mazzocco | |
| 4,715,373 A | 12/1987 | Mazzocco et al. | |
| 4,747,404 A | 5/1988 | Jampel et al. | |

(Continued)

FOREIGN PATENT DOCUMENTS

CN 1234732 A 11/1999
CN 1456134 A 11/2003

(Continued)

*Primary Examiner* — Gary Jackson
*Assistant Examiner* — Katrina Stransky
(74) *Attorney, Agent, or Firm* — Henricks, Slavin & Holmes LLP

(57) ABSTRACT

An intraocular lens inserting instrument capable of folding a lens and pressing it by a plunger to discharge it into an eye and alternatively capable of taking out the folded lens by tweezers. The intraocular lens inserting instrument for inserting a foldable intraocular lens into an eye has a tubular body for allowing the intraocular lens to pass through it and introducing it into the eye, and a plunger for pressing the intraocular lens to discharge it into the eye, wherein the intraocular lens is folded by a folding member provided at a lens placing section. The lens placing section has an open/close lid so that the folded intraocular lens is accessible to be held by the tweezers.

15 Claims, 9 Drawing Sheets

(56) References Cited

U.S. PATENT DOCUMENTS

| | | | |
|---|---|---|---|
| 4,750,498 A | 6/1988 | Graham | |
| 4,759,359 A | 7/1988 | Willis et al. | |
| 4,763,650 A | 8/1988 | Hauser | |
| 4,765,329 A | 8/1988 | Cumming et al. | |
| 4,769,034 A | 9/1988 | Poley | |
| 4,781,719 A | 11/1988 | Kelman | |
| 4,787,904 A | 11/1988 | Severin | |
| 4,819,631 A | 4/1989 | Poley | |
| 4,834,094 A | 5/1989 | Patton | |
| 4,836,201 A | 6/1989 | Patton | |
| 4,862,885 A | 9/1989 | Cumming | |
| 4,880,000 A | 11/1989 | Holmes et al. | |
| 4,919,130 A | 4/1990 | Stoy et al. | |
| 4,934,363 A | 6/1990 | Smith et al. | |
| 4,955,889 A | 9/1990 | Van Gent | |
| 4,976,716 A | 12/1990 | Cumming | |
| 4,988,352 A | 1/1991 | Poley | |
| 4,994,028 A | 2/1991 | Leonard et al. | |
| 5,066,297 A * | 11/1991 | Cumming | 606/107 |
| 5,098,439 A | 3/1992 | Hill et al. | |
| 5,123,905 A | 6/1992 | Kelman | |
| 5,139,501 A | 8/1992 | Klaas | |
| 5,171,241 A | 12/1992 | Buboltz et al. | |
| 5,176,686 A | 1/1993 | Poley | |
| 5,190,552 A | 3/1993 | Kelman | |
| 5,190,553 A | 3/1993 | Kanert et al. | |
| 5,222,972 A | 6/1993 | Hill et al. | |
| 5,242,450 A | 9/1993 | McDonald | |
| 5,275,604 A | 1/1994 | Rheinish et al. | |
| 5,281,227 A | 1/1994 | Sussman | |
| 5,304,182 A | 4/1994 | Rheinish et al. | |
| 5,354,333 A | 10/1994 | Kammann et al. | |
| 5,395,378 A | 3/1995 | McDonald | |
| 5,425,734 A | 6/1995 | Blake | |
| 5,454,818 A | 10/1995 | Hambleton et al. | |
| 5,468,246 A | 11/1995 | Blake | |
| 5,474,562 A | 12/1995 | Orchowski et al. | |
| 5,494,484 A | 2/1996 | Feingold | |
| 5,496,328 A * | 3/1996 | Nakajima et al. | 606/107 |
| 5,499,987 A | 3/1996 | Feingold | |
| 5,562,676 A | 10/1996 | Brady et al. | |
| 5,571,113 A | 11/1996 | McDonald | |
| 5,578,042 A | 11/1996 | Cumming | |
| 5,582,613 A | 12/1996 | Brady | |
| 5,582,614 A | 12/1996 | Feingold | |
| 5,584,304 A | 12/1996 | Brady | |
| 5,616,148 A | 4/1997 | Eagles et al. | |
| 5,620,450 A | 4/1997 | Eagles et al. | |
| 5,643,275 A | 7/1997 | Blake | |
| 5,643,276 A | 7/1997 | Zaleski | |
| 5,653,715 A | 8/1997 | Reich et al. | |
| 5,653,753 A | 8/1997 | Brady et al. | |
| 5,702,402 A | 12/1997 | Brady | |
| 5,702,441 A | 12/1997 | Zhou | |
| 5,716,364 A | 2/1998 | Makker et al. | |
| 5,728,102 A | 3/1998 | Feingold et al. | |
| 5,735,858 A | 4/1998 | Makker et al. | |
| 5,766,181 A | 6/1998 | Chambers et al. | |
| 5,772,666 A | 6/1998 | Feingold et al. | |
| 5,772,667 A | 6/1998 | Blake | |
| 5,776,138 A | 7/1998 | Vidal et al. | |
| 5,800,442 A | 9/1998 | Wolf et al. | |
| 5,803,925 A | 9/1998 | Yang et al. | |
| 5,807,400 A | 9/1998 | Chambers et al. | |
| 5,810,833 A | 9/1998 | Brady et al. | |
| 5,810,834 A | 9/1998 | Heyman | |
| 5,860,984 A | 1/1999 | Chambers et al. | |
| 5,860,986 A | 1/1999 | Reich et al. | |
| 5,868,751 A | 2/1999 | Feingold | |
| 5,868,752 A | 2/1999 | Makker et al. | |
| 5,873,879 A | 2/1999 | Figueroa et al. | |
| 5,876,406 A | 3/1999 | Wolf et al. | |
| 5,876,407 A | 3/1999 | Makker et al. | |
| 5,876,440 A | 3/1999 | Feingold | |
| 5,891,152 A | 4/1999 | Feingold | |
| 5,902,307 A | 5/1999 | Feingold et al. | |
| 5,919,197 A | 7/1999 | McDonald | |
| 5,921,989 A | 7/1999 | Deacon et al. | |
| 5,928,245 A | 7/1999 | Wolf et al. | |
| 5,941,886 A | 8/1999 | Feingold | |
| 5,942,277 A | 8/1999 | Makker et al. | |
| 5,944,725 A | 8/1999 | Cicenas et al. | |
| 5,947,974 A | 9/1999 | Brady et al. | |
| 5,947,975 A | 9/1999 | Kikuchi et al. | |
| 5,957,748 A * | 9/1999 | Ichiha | 450/58 |
| 6,001,107 A | 12/1999 | Feingold | |
| 6,010,510 A | 1/2000 | Brown et al. | |
| 6,022,358 A | 2/2000 | Wolf et al. | |
| 6,048,348 A | 4/2000 | Chambers et al. | |
| 6,051,000 A | 4/2000 | Heyman | |
| 6,056,757 A | 5/2000 | Feingold et al. | |
| 6,056,758 A | 5/2000 | Vidal et al. | |
| 6,059,791 A | 5/2000 | Chambers | |
| 6,074,397 A | 6/2000 | Chambers et al. | |
| 6,083,230 A | 7/2000 | Makker et al. | |
| 6,093,193 A | 7/2000 | Makker et al. | |
| 6,129,733 A | 10/2000 | Brady et al. | |
| 6,142,999 A | 11/2000 | Brady et al. | |
| 6,143,000 A | 11/2000 | Feingold | |
| 6,162,229 A | 12/2000 | Feingold et al. | |
| 6,174,315 B1 | 1/2001 | Chambers et al. | |
| 6,214,015 B1 | 4/2001 | Reich et al. | |
| 6,241,737 B1 | 6/2001 | Feingold | |
| 6,248,111 B1 | 6/2001 | Glick et al. | |
| 6,251,114 B1 | 6/2001 | Farmer et al. | |
| 6,254,607 B1 | 7/2001 | Makker et al. | |
| 6,267,768 B1 | 7/2001 | Deacon | |
| 6,283,975 B1 | 9/2001 | Glick et al. | |
| 6,283,976 B1 | 9/2001 | Portney | |
| 6,312,433 B1 | 11/2001 | Butts | |
| 6,334,862 B1 | 1/2002 | Vidal et al. | |
| 6,336,932 B1 | 1/2002 | Figueroa et al. | |
| 6,355,046 B2 | 3/2002 | Kikuchi et al. | |
| 6,371,960 B2 | 4/2002 | Heyman et al. | |
| 6,386,357 B1 * | 5/2002 | Egawa | 206/5.1 |
| 6,387,101 B1 | 5/2002 | Butts et al. | |
| 6,398,788 B1 | 6/2002 | Makker et al. | |
| 6,406,481 B2 | 6/2002 | Feingold et al. | |
| 6,428,545 B2 | 8/2002 | Portney | |
| 6,447,519 B1 | 9/2002 | Brady et al. | |
| 6,447,520 B1 | 9/2002 | Ott et al. | |
| 6,468,282 B2 | 10/2002 | Kikuchi et al. | |
| 6,471,708 B2 | 10/2002 | Green | |
| 6,491,697 B1 * | 12/2002 | Clark et al. | 606/107 |
| 6,497,708 B1 | 12/2002 | Cumming | |
| 6,500,181 B1 | 12/2002 | Portney | |
| 6,506,195 B2 | 1/2003 | Chambers et al. | |
| 6,537,283 B2 | 3/2003 | Van Noy | |
| 6,540,754 B2 | 4/2003 | Brady | |
| 6,554,839 B2 | 4/2003 | Brady | |
| 6,558,395 B2 | 5/2003 | Hjertman et al. | |
| 6,607,537 B1 | 8/2003 | Binder | |
| 6,629,979 B1 | 10/2003 | Feingold | |
| 6,666,871 B2 | 12/2003 | Kikuchi et al. | |
| 6,679,891 B2 | 1/2004 | Makker et al. | |
| 6,685,740 B2 | 2/2004 | Figueroa et al. | |
| 6,712,848 B1 | 3/2004 | Wolf et al. | |
| 6,723,104 B2 | 4/2004 | Ott | |
| 6,733,507 B2 | 5/2004 | McNicholas et al. | |
| 6,793,674 B2 | 9/2004 | Zapata | |
| 6,858,033 B2 | 2/2005 | Kobayashi | |
| 6,921,405 B2 | 7/2005 | Feingold et al. | |
| 6,923,815 B2 * | 8/2005 | Brady et al. | 606/107 |
| 6,976,989 B1 | 12/2005 | Vincent | |
| 7,014,641 B2 | 3/2006 | Kobayashi et al. | |
| 7,025,782 B2 | 4/2006 | Kobayashi et al. | |
| 7,033,366 B2 | 4/2006 | Brady | |
| 7,037,312 B2 | 5/2006 | Kikuchi et al. | |
| 7,074,227 B2 | 7/2006 | Portney | |
| 7,097,649 B2 | 8/2006 | Meyer | |
| 7,131,976 B2 | 11/2006 | Kobayashi et al. | |
| 7,156,854 B2 | 1/2007 | Brown et al. | |
| 7,348,038 B2 | 3/2008 | Makker et al. | |
| 7,422,604 B2 | 9/2008 | Vaquero et al. | |

| | | | | | | |
|---|---|---|---|---|---|---|
| 7,429,263 | B2 | 9/2008 | Vaquero et al. | EP | 1832247 A1 | 9/2007 |
| 7,458,976 | B2 | 12/2008 | Peterson et al. | EP | 1338254 | 12/2008 |
| 7,476,230 | B2 | 1/2009 | Ohno et al. | FR | 2749752 A1 | 12/1997 |
| 7,494,505 | B2 | 2/2009 | Kappelhof et al. | JP | 63-197453 A | 8/1988 |
| 7,645,300 | B2 | 1/2010 | Tsai | JP | 4-212350 A | 8/1992 |
| 8,273,122 | B2 | 9/2012 | Anderson | JP | 5-103808 | 4/1993 |
| 8,382,769 | B2 | 2/2013 | Inoue | JP | 5-103809 | 4/1993 |
| 8,460,311 | B2 | 6/2013 | Ishii | JP | 8-024282 A | 1/1996 |
| 2001/0007942 | A1 | 7/2001 | Kikuchi et al. | JP | 8-505540 | 6/1996 |
| 2002/0103490 | A1 | 8/2002 | Brady | JP | 9-506285 A | 6/1997 |
| 2002/0151904 | A1 | 10/2002 | Feingold et al. | JP | 11-113939 A | 4/1999 |
| 2002/0165610 | A1 | 11/2002 | Waldock | JP | 11-506357 | 6/1999 |
| 2002/0193805 | A1 | 12/2002 | Ott et al. | JP | 2000-516487 A | 12/2000 |
| 2003/0036765 | A1 | 2/2003 | Van Noy | JP | 2000-516488 A | 12/2000 |
| 2003/0040755 | A1 | 2/2003 | Meyer | JP | 2001-502563 A | 2/2001 |
| 2003/0050647 | A1 | 3/2003 | Brady | JP | 2001-104347 A | 4/2001 |
| 2003/0139749 | A1 | 7/2003 | Kikuchi et al. | JP | 2002-516709 A | 6/2002 |
| 2003/0181921 | A1 | 9/2003 | Jeannin | JP | 2002-355268 A | 12/2002 |
| 2003/0195522 | A1 | 10/2003 | McNicholas | JP | 2002-541912 A | 12/2002 |
| 2003/0212406 | A1 | 11/2003 | Kobayashi et al. | JP | 2003-144480 A | 5/2003 |
| 2003/0212407 | A1 | 11/2003 | Kikuchi | JP | 3412106 B2 | 6/2003 |
| 2003/0212409 | A1 | 11/2003 | Kobayashi et al. | JP | 2003-210498 A | 7/2003 |
| 2004/0111094 | A1 | 6/2004 | Meyer | JP | 2003-325569 A | 11/2003 |
| 2004/0117012 | A1 | 6/2004 | Vincent | JP | 2003-325570 A | 11/2003 |
| 2004/0238392 | A1* | 12/2004 | Peterson et al. ............. 206/438 | JP | 2003-325572 A | 11/2003 |
| 2004/0243141 | A1* | 12/2004 | Brown et al. .................. 606/107 | JP | 2004-024854 A | 1/2004 |
| 2005/0033308 | A1 | 2/2005 | Callahan et al. | JP | 2004-188194 A | 7/2004 |
| 2005/0049605 | A1 | 3/2005 | Vaquero et al. | JP | 2004-351196 A | 12/2004 |
| 2005/0049606 | A1 | 3/2005 | Vaquero et al. | JP | 2006-181269 A | 7/2006 |
| 2005/0125000 | A1 | 6/2005 | Tourrette et al. | JP | 2006-297146 A | 11/2006 |
| 2005/0182419 | A1 | 8/2005 | Tsai | JP | 2006-333924 A | 12/2006 |
| 2005/0222578 | A1 | 10/2005 | Vaquero | JP | 2006-333981 A | 12/2006 |
| 2005/0261703 | A1 | 11/2005 | Feingold et al. | JP | 2007-503872 A | 3/2007 |
| 2006/0085013 | A1 | 4/2006 | Dusek | JP | 2007-152010 A | 6/2007 |
| 2006/0167466 | A1* | 7/2006 | Dusek ............................ 606/107 | JP | 2007-181604 A | 7/2007 |
| 2006/0293694 | A1 | 12/2006 | Futamura | JP | 2007-526091 A | 9/2007 |
| 2008/0033449 | A1 | 2/2008 | Cole et al. | JP | 2008-521535 A | 6/2008 |
| 2008/0058830 | A1 | 3/2008 | Cole et al. | JP | 2008-212689 A | 9/2008 |
| 2008/0086146 | A1 | 4/2008 | Ishii et al. | WO | WO9407436 A1 | 4/1994 |
| 2008/0097459 | A1 | 4/2008 | Kammerlander et al. | WO | WO9513022 A1 | 5/1995 |
| 2008/0221584 | A1 | 9/2008 | Downer | WO | WO9628122 A1 | 9/1996 |
| 2009/0036898 | A1 | 2/2009 | Ichinohe | WO | WO9715253 A1 | 5/1997 |
| 2009/0043313 | A1 | 2/2009 | Ichinohe | WO | 98/12969 A1 | 4/1998 |
| 2009/0112223 | A1 | 4/2009 | Downer et al. | WO | WO0045746 A1 | 8/2000 |
| 2009/0216244 | A1 | 8/2009 | Pynson | WO | WO0062712 A1 | 10/2000 |
| 2009/0248031 | A1 | 10/2009 | Ichinohe | WO | WO02071982 A1 | 9/2002 |
| 2010/0161049 | A1 | 6/2010 | Inoue | WO | 02/086322 A2 | 10/2002 |
| 2010/0185206 | A1 | 7/2010 | Ichinohe et al. | WO | 02/096322 A1 | 12/2002 |
| 2010/0217273 | A1 | 8/2010 | Someya et al. | WO | WO2005023154 A1 | 3/2005 |
| 2010/0286704 | A1 | 11/2010 | Ichinohe et al. | WO | WO2005070341 A1 | 8/2005 |
| 2011/0082463 | A1 | 4/2011 | Inoue | WO | WO2005084588 A1 | 9/2005 |
| 2011/0098717 | A1 | 4/2011 | Inoue | WO | WO2006070628 A1 | 7/2006 |
| 2011/0264101 | A1 | 10/2011 | Inoue et al. | WO | WO2006080191 A1 | 8/2006 |
| 2011/0270264 | A1 | 11/2011 | Shoji et al. | WO | WO2006090531 A1 | 8/2006 |
| 2011/0288557 | A1 | 11/2011 | Kudo et al. | WO | WO2007037223 A1 | 4/2007 |
| 2012/0022549 | A1 | 1/2012 | Someya et al. | WO | WO2007097221 A1 | 4/2007 |
| 2012/0071887 | A1 | 3/2012 | Ichinohe et al. | WO | WO2007080869 A1 | 7/2007 |
| 2013/0006259 | A1 | 1/2013 | Sanger | WO | WO2008149794 A1 | 12/2008 |
| 2013/0018460 | A1 | 1/2013 | Anderson | WO | WO2008149795 A1 | 12/2008 |
| | | | | WO | WO2009058929 A1 | 7/2009 |
| | | | | WO | WO2009148091 A1 | 12/2009 |

FOREIGN PATENT DOCUMENTS

| | | |
|---|---|---|
| DE | 3610925 | 10/1987 |
| DE | 4110278 | 10/1992 |
| EP | 0363213 | 4/1990 |
| EP | 0727966 | 9/2003 |

| | | |
|---|---|---|
| WO | WO2011126144 A1 | 10/2011 |
| WO | WO2011155636 A1 | 12/2011 |

* cited by examiner (a)

(b)

INTRAOCULAR LENS INSERTING INSTRUMENT

CROSS-REFERENCE TO RELATED APPLICATIONS

This application is the national phase under 35 U.S.C. §371 of PCT International Application No. PCT/JP2006/300291, which has an International filing date of Jan. 12, 2006, designated in the United States and claims priority from Japanese Patent Application No. 2005-049700, filed Feb. 24, 2005. International Patent Application No. PCT/JP2006/300291 and Japanese Patent Application No. 2005-049700 are incorporated by reference herein in their entireties.

FIELD OF THE INVENTION

The present invention relates to an intraocular lens inserting instrument that inserts an intraocular lens into an eye in place of a lens removed by a cataract operation, and more particularly to an intraocular lens inserting instrument capable of grasping a folded intraocular lens by tweezers and inserting said intraocular lens into an eye.

DESCRIPTION OF THE RELATED ART

In cataract operations, the method of removing an opacified lens by phacoemulsification and implanting an artificial intraocular lens after the opacified lens has been removed is widely employed. There are two types of implanted intraocular lens; these being a hard intraocular lens with the optical area made of a hard material, such as polymethylmethacrylate (PMMA), and a soft intraocular lens made of a soft material such as silicone elastomer, soft acrylic, or hydrogel. When using a hard intraocular lens, the intraocular lens must be inserted through an incision in the cornea or sclera that is of the same or slightly wider width than the diameter of the optical area. On the other hand, when using a soft intraocular lens, folding of the optical area allows the intraocular lens to be inserted into the eye through an even smaller incision. Further, performing the operation with a smaller incision makes it possible to reduce the risk of post-surgery corneal astigmatism and infection. For such reasons, there has been a trend in recent years to favor the use of soft intraocular lens.

Methods for inserting a soft intraocular lens in an eye include the method of using tweezers to insert a folded intraocular lens directly into an eye and the method of using a special insertion instrument called an injector. Using a special injector makes it possible to fold the intraocular lens smaller than when it is folded by tweezers. This makes it possible to insert an intraocular lens (hereinafter referred to as simply a "lens") into an eye through an incision of 3 mm or smaller.

In addition, preset injectors having the lens set in the injector in advance to eliminate the risk of contamination by microbes during lens handling and of possible operational mistakes during lens handling have recently been announced. Further, some preset injectors are provided with a lens holding mechanism that holds the lens inside the injector in an immovable state that does not stress the optical area and with a lens moving mechanism that moves the lens to a position where it can be pushed out by an discharge device so as to transfer the lens from the lens immovable state during shipment to the lens movable state during use (For example, see Japanese Patent Application (JP-A) Laid Open Nos. 2003-325570 and 2003-325572, which are incorporated by reference herein in their entireties).

However, a preset injector disclosed in the above patent documents must move the lens from the stationary position to a usable position during its use, and the risk of problems accompanying the movement operation cannot be eliminated. Further, because the injector has a mechanism that moves the lens to a usable position and begins pushing with the optical area being nearly undistorted, the discharge device is required to have a long movement distance. This increases the possibility of a problem occurring during operation and creates structural limitations, such as making the overall length of the injector longer. For this reason, by providing a mechanism to first fold the intraocular lens in a lens placing section so that the lens is deformed to a degree and then to start to move it into the eye, it is possible to shorten the movement distance inside the lens tube to decrease accidents occurring during the moving process and improve usability by shortening the overall length of the injector. In view of the above, an intraocular lens inserting instrument provided with a mechanism for transversely compressing a flexible intraocular lens to obtain a small cross-sectional area has been disclosed (For example, see Japanese Patent Application Laid-Open (JP-A) No. 2001-502563, which is incorporated by reference herein in its entirety).

However, a characteristic of the invention disclosed in JP-A 2001-502563 is that it is provided with retainers to maintain the side edges of the lens in a substantially planar orientation so as not to damage the inside of the eye when releasing the intraocular lens in the eye from a compressed state. In this state, if the intraocular lens is pressed against the fine areas of the lens placing section and narrow tube member, a very high load is placed on the lens, which could damage the lens. In addition, the lens is completely enclosed in the tube member, so it is not possible to remove, after deformation, a lens that has been deformed inside the inserting instrument.

However, there are cases during surgery when, for whatever reason, such as when the lens must be sewn in place or when the surgeon prefers to use tweezers to insert the lens, it is necessary to use tweezers to insert the intraocular lens into the eye. In such a case, there will be taken steps for removing a lens that has been set in an injector from inside the injector and then folding the lens in an appropriate manner, and inserting it into the eye using tweezers. Using such a multiple step operation, however, increases the risk of contaminating the eye with foreign matter or microbes and the possibility of dropping or damaging the lens through handling mistakes. In the case of a preset injector in particular, the injector is shipped with the lens set inside, and none of the currently commercially available preset injectors were designed with the intention of using tweezers to remove the lens and, therefore, are not provided with a mechanism for safely removing the intraocular lens without breaking the injector.

BRIEF SUMMARY OF THE INVENTION

For this reason, it is desirable to realize an intraocular lens inserting instrument that allows for both usage methods depending on the surgical method employed. An object of the present invention is to provide a function for performing a simple operation to fold a lens set in the lens placing section of a preset injector in which an intraocular lens has been set in the injector in advance. A further object of the present invention, in the case where the injector is used for direct insertion into an eye, is to provide a lens inserting instrument where an intraocular lens is discharged using a plunger to be inserted into an eye after the intraocular lens has been folded in the lens placing section, and, in the case where tweezers are used to hold the lens and insert the lens into an eye, is to provide a lens inserting instrument where the lens placing section can be opened by an opening mechanism provided in the top wall or part of the lens placing section before or after the lens has been folded to thereby allow the folded lens to be removed in the folded state using tweezers. Therefore, the present invention most preferably applies to preset injectors that are shipped with a lens set in advance.

Further, the present invention also applies to injectors in which the lens and injector are supplied in separate packaging, and in this case, the injector can be used to insert the lens, but even after the lens has been set in the injector, switching to the lens insertion operation using tweezers is also possible to meet urgent surgical requirements.

The present invention according to a first aspect concerns an intraocular lens inserting instrument for inserting a folded intraocular lens into an eye, characterized in comprising a tubular body through which the intraocular lens is guided to the eye, a plunger that presses and discharges the intraocular lens into the eye, a folding member that folds the intraocular lens in a lens placing section provided in the body, wherein the intraocular lens is removable in the lens placing section.

The present invention according to a second aspect is characterized by a means for folding in two the intraocular lens in the intraocular lens inserting instrument of the first aspect.

The present invention according to a third aspect is characterized by providing an open/close lid in the lens placing section that is integrated with or separate from the body of an intraocular lens inserting instrument according to the first or second aspect.

The present invention according to a fourth aspect is characterized by the open/close lid being attached by a hinge to the body of an intraocular lens inserting instrument according to the third aspect.

The present invention according to a fifth aspect is characterized by the intraocular lens folded in the lens placing section being capable of being grasped by tweezers in an intraocular lens inserting instrument according to any one of the first to fourth aspects.

The present invention according to a sixth aspect is characterized by providing two folding members in the lens placing section wherein the folding members are joined by a plate spring and the folding members are provided with a protrusion that opposes the bias force of the plate spring, to maintain the position of the folding members of an intraocular lens inserting instrument according to any one of the first to fifth aspects.

The present invention according to a seventh aspect is characterized by providing a locking mechanism in the folding members wherein the intraocular lens cannot be folded unless the locking mechanism is unlocked in an intraocular lens inserting instrument according to any one of the first to fifth aspects.

The intraocular lens inserting instrument according to the first aspect enables an intraocular lens to be implanted in an eye using an injector with the intraocular lens set in advance, while also allowing the folded intraocular lens to be grasped by tweezers and implanted in an eye when necessary after the intraocular lens has been folded.

The intraocular lens inserting instrument according to the second aspect enables an intraocular lens to be folded in two, thus allowing the intraocular lens to be easily grasped by tweezers.

The intraocular lens inserting instrument according to the third aspect has an open/close lid through which tweezers can be used to grasp the folded intraocular lens.

The intraocular lens inserting instrument according to the fourth aspect has a hinge that fastens the open/close lid to the body so that the open/close lid does not fall from the body.

The intraocular lens inserting instrument according to the fifth aspect allows, when necessary, the intraocular lens to be grasped by tweezers and implanted into an eye after the intraocular lens has been folded in a lens placing section.

The intraocular lens inserting instrument according to the sixth aspect has two folding members joined by a plate spring, thus enabling an operating force of suitable magnitude to be obtained. Further, protrusions that can latch with the body are provided on the folding members, thus opposing the bias force of the spring plate to maintain the position of the folding members.

The intraocular lens inserting instrument according to the seventh aspect provides a locking mechanism in the folding members that prevents the intraocular lens from being folded unless the locking mechanism is unlocked, thus preventing unintentional deformation of the intraocular lens.

BRIEF DESCRIPTION OF THE DRAWINGS

FIGS. 11a and 11b each provide an oblique perspective view of the third embodiment as viewed from the D-D direction of FIG. 10, in which FIG. 11a shows the preset state and FIG. 11b shows the state after the lens is folded.

FIGS. 12a and 12b each provide an oblique perspective view of the third embodiment as viewed from the D-D direction of FIG. 10 in which FIG. 12a shows the lens being discharged by a plunger and FIG. 12b shows the lens being ready to be grasped by tweezers.

DETAILED DESCRIPTION OF THE INVENTION

Figure 1:
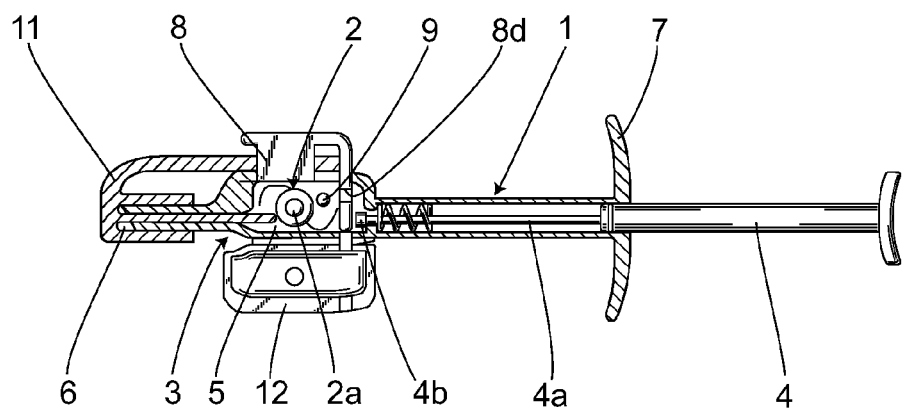
FIG. 1 is a drawing showing the open/close lid of the intraocular lens inserting instrument in an open state according to a first embodiment of the present invention.
Figure 2:
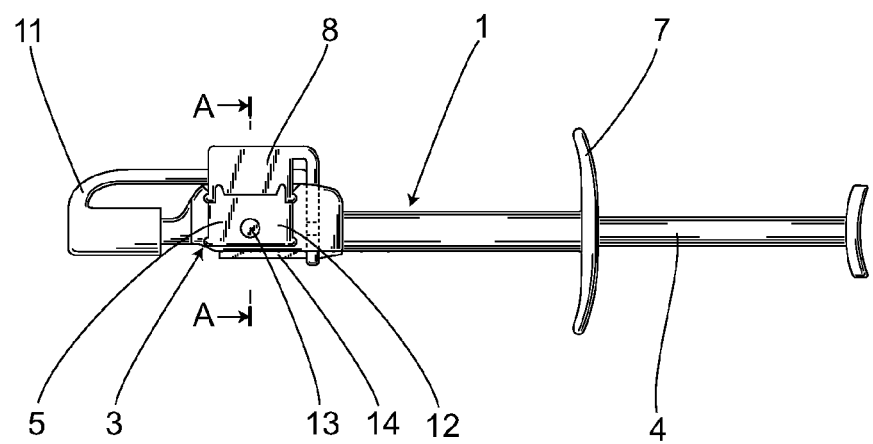
FIG. 2 is an outline view showing the open/close lid of the intraocular lens inserting instrument in a closed state according to the first embodiment of the present invention.
Figure 3A:
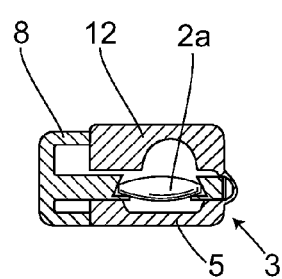
FIG. 3 is a cross-section view from the A-A direction of FIG. 2 in which 3a shows the preset state, 3b shows the state after the lens is folded, and 3c shows removal using tweezers.
Figure 3B:
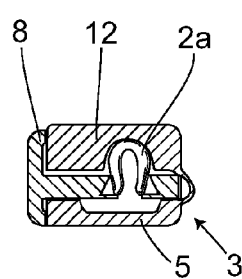
Figure 3C:
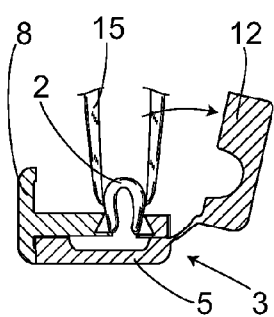

The following reference elements are described in further detail below in reference to the drawing figures:

1 Intraocular lens inserting instrument (injector)
2 Intraocular lens (lens)
3 Body
4 Plunger
5 Lens placing section
8 Folding member
8f Protrusion
12 Open/close lid
14 Hinge
15 Tweezers
8g, 16c Locking mechanism
17 Plate spring The present invention is described with reference to the drawings. FIG. 1 to FIG. 3 are diagrams showing an intraocular lens inserting instrument according to a the first embodiment of the present invention. FIG. 1 provides a cross-section view showing the open/close lid in an open position and nozzle cap attached. The intraocular lens inserting instrument 1 is an intraocular lens inserting instrument 1 for inserting a foldable, flexible intraocular lens 2 in an eye and comprises a tubular body 3 through which the afore-mentioned intraocular lens 2 is passed and guided into the eye, a plunger 4 for discharging the compressed afore-mentioned intraocular lens 2 into an eye, folding members 8 for folding into two the intraocular lens 2 in a lens placing section 5 provided in the afore-mentioned body 3, and a means for removing the intraocular lens 2 from the afore-mentioned lens placing section 5.

The tubular body 3 is also called the hand piece, and a lens placing section 5 is provided in the midst of the tubular body 3. Further, the inside diameter of the end 6 of the tubular shape is narrowly constricted and this end 6 is such that it enables the intraocular lens 2 to be implanted by inserting the lens into eye through an incision. In addition, the surgeon side of the tubular body 3 is provided with a grasping section 7 and the inside of the tubular body 3 is mounted with a freely sliding plunger 4 that discharges the intraocular lens 2. Further, the folding members 8 that fold the intraocular lens 2 inside the lens placing section 5 are mounted in the transverse direction to the plunger shaft 4a such that the folding members 8 can move parallel above the lens placing section 5. When setting the lens 2, the folding members 8 are pulled out in the outer lateral direction to set the lens 2. When the folding members 8 are pulled all the way in the outer lateral direction, a space slightly larger than the outside diameter of the lens optical area 2a is obtained in the lens placing section 5 to allow the lens 2 to be set without applying excessive stress to the optical area 2a of the lens 2.

In addition, when the folding members 8 are pulled in the outer lateral direction, the plunger end 4b is constructed such that it butts against the sides of the folding members 8 to restrict the lens 2 from being discharged due to a plunger 4 operation mistake, etc. Note that the lens placing section 5 is provided with a position restriction protrusion 9 to restrict the movement of the lens 2.

Further, during surgery the tubular end 6 is inserted into the eye, so it must be kept sterile at all times. For this reason, a nozzle cap 11 is placed on the tip forming the nozzle 6 to protect the same. The nozzle cap 11 protects the nozzle 6 and also functions to restrict the pushing motion of the afore-mentioned folding members 8. More specifically, the construction is such that the folding members 8 cannot be pushed unless the nozzle cap 11 is removed. Therefore, this construction prevents the lens 2 from being folded at an unsuitable time due to an operational mistake, etc.

FIG. 2 is an external view of the injector 1 showing the state where an open/close lid 12 is closed after the lens 2 is set. The open/close lid 12 is provided in the lens placing section 5 integrated with or separate from the body 3, and closing the open/close lid 12 after the lens 2 is set fixes the intraocular lens 2 in the lens placing section 5 to allow the injector 1 to be transported, etc. In addition, the open/close lid 12 is provided with a hole 13 for inspections to allow the state of the lens 2 set in the lens placing section 5 to be easily viewed from outside even if the open/close lid 12 is closed. In this embodiment the open/close lid 12 is integrated with the body 3 and opens and closes by a hinge 14 made from plastic material.

FIG. 3 is a cross-section view showing FIG. 2 from the A-A direction wherein (a) shows the lens 2 in the preset state and (b) shows the lens 2 in the state after folding. Further, (c) shows the folded lens 2 being removed by tweezers (15). In the preset state shown in (a), the lens 2 is held in place such that it cannot move freely but that excessive force is not applied to the optical area 2a. Therefore, there is no negative effect on the optical properties of the lens 2 even when stored for a long time in the preset state. In addition, even if the plunger 4 is mistakenly operated, the movement of the plunger 4 will be restricted by butting against the folding members 8 as long as the folding members 8 are not pushed in to prevent the intraocular lens 2 from being discharged while in the preset state shown in (a). Further, the folding members 8 cannot be pushed in as long as the nozzle cap 11 is not removed to prevent the intraocular lens 2 from being folded.

During the surgery, when using the injector 1 to insert the intraocular lens 2 in the eye, the nozzle cap 11 is removed before pushing in the folding members 8 to deform and fold the intraocular lens 2 stored in the lens placing section 5. Specifically, when pushing in the folding members 8 as shown in (b), the optical area 2a of the intraocular lens 2 is compressed by the inner wall of the body 3 and the folding members 8 to fold the optical area 2a into a U-shape. Then the tip that forms the nozzle 6 is inserted into the eye through the incision in the eyeball and then the intraocular lens 2 is discharged by the plunger 4 and implanted in the eye. Note that the plunger is constructed such that when the folding members 8 are pushed in and the intraocular lens 2 is in the folded position, the center of the plunger through hole 8d provided in the folding members 8 aligns with the shaft center of the plunger shaft 4a to allow the plunger 4 to be pressed to compress and move the intraocular lens 2.

On the other hand, there are cases where the surgeon determines that it would be better to use tweezers 15 to grasp the intraocular lens 2 and insert it into the eye than to use the injector 1 to directly implant the lens 2 into the eye. In such a case, as shown by (c), after the folding members 8 fold the intraocular lens 2, the open/close lid 12 is opened and the tweezers 15 are used to grasp the folded optical area 2a and insert it into the eye. Therefore, according to the present invention, it is both possible to use the injector 1 to implant the intraocular lens 2 in the eye, or, when necessary, to use the tweezers 15 to grasp the folded intraocular lens 2 and implant it in the eye.

Figure 4:
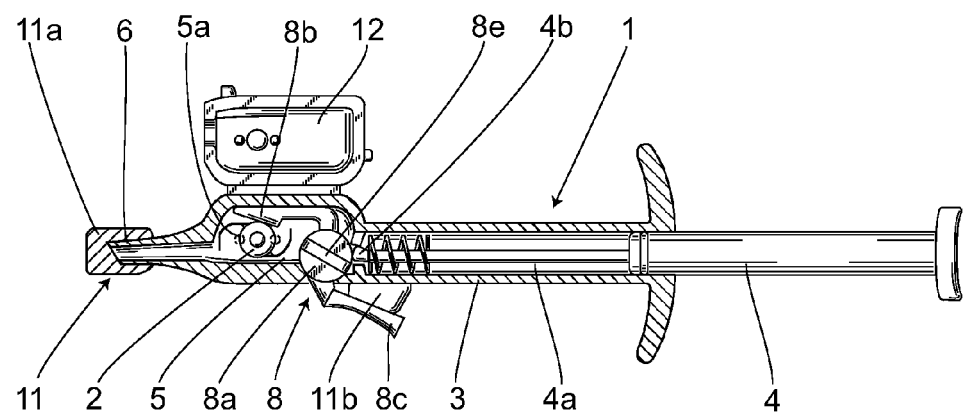
FIG. 4 is a drawing showing the open/close lid of the intraocular lens inserting instrument in an opened state according to a second embodiment of the present invention.

FIG. 4 to FIG. 8 show the intraocular lens inserting instrument 1 according to the second embodiment of the present invention, and FIG. 4 is a drawing of the open/close lid 12 in the open position. The detailed construction of the folding members 8, nozzle cap 11, and protective cover 16 of this embodiment differs from the afore-mentioned first embodiment. Therefore, the explanation of the areas in common with the first embodiment is omitted and the folding members 8, nozzle cap 11, and protective cover 16 having a differing construction are explained.

Figure 5:
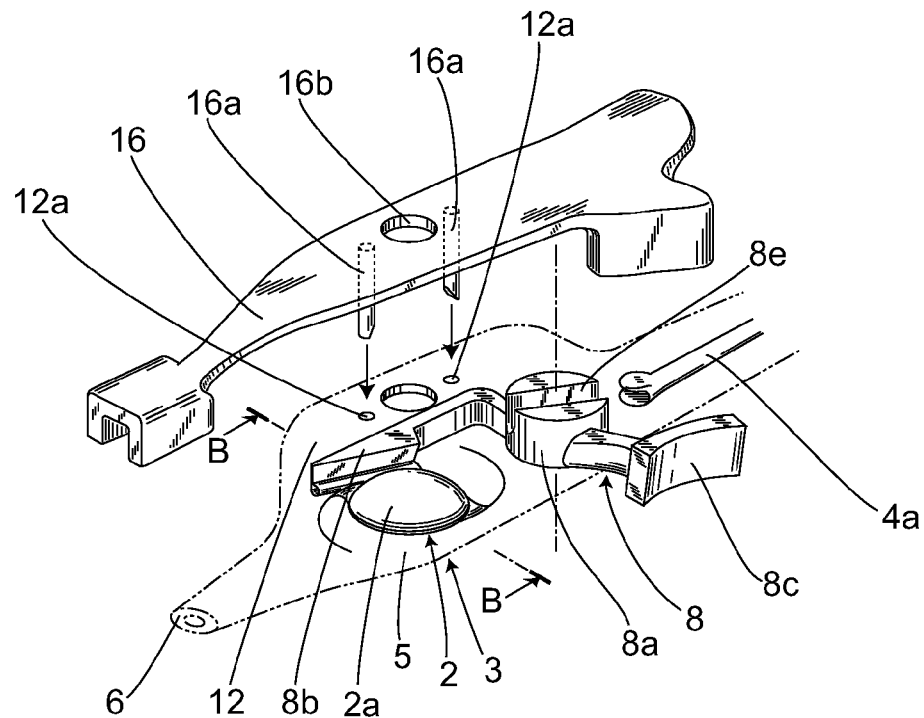
FIG. 5 is an oblique perspective view showing the second embodiment including a removable protective cover.

The folding members 8 according to this embodiment are provided with a rotating boss 8a in the lens placing section 5, and the boss 8a is provided with an integrated compression member 8b positioned in the lens placing section 5 and an operation member 8c that extends outward from the body 3. Further, as shown in FIG. 5, when the intraocular lens 2 is set in the lens placing section 5, the operation member 8c is rotated outward from the body 3 to obtain a wide space in the lens placing section 5 and set the lens 2. In this state, the direction of the through groove 8e provided in the boss 8a and the direction of the plunger shaft 4a do not align to prevent the intraocular lens 2 from being compressed by the plunger shaft 4a even by an operational mistake because even if the plunger 4 is pressed, the end 4b of the plunger shaft 4a is restricted by butting against the side of the boss 8a.

In addition, the nozzle cap 11 according to this embodiment, as shown in FIG. 4, comprises a cap 11a that covers the end of the nozzle 6 and a press holder 11b that are formed as a single unit. Here, the press holder 11b is positioned between the outer wall of the body 3 and the operation member 8c of the afore-mentioned folding members 8 to prevent the operation member 8c from operating as long as the press holder 11b is not removed.

Further, as shown in FIG. 5, a protective cover 16 that protects the nozzle 6 and the entire lens placing section 5 can be provided. The bottom of the protective cover 16 is provided with two integrated protrusions 16a such that when the protective cover 16 is placed on the body 3 and the afore-mentioned protrusions 16a are inserted into the holes 12a provided in the open/close lid 12, the protrusions 16a extend to near the outer edge of the optical area 2a of the lens 2. Therefore, when the protective cover 16 is mounted on the body 3, it restricts the movement of the lens 2 in the lens placing section 5. Note that the protective cover 16 is also provided with an inspection hole 16b for viewing the state of the lens 2 placed in a position corresponding to the center of the lens optical area 2a.

Figure 6:
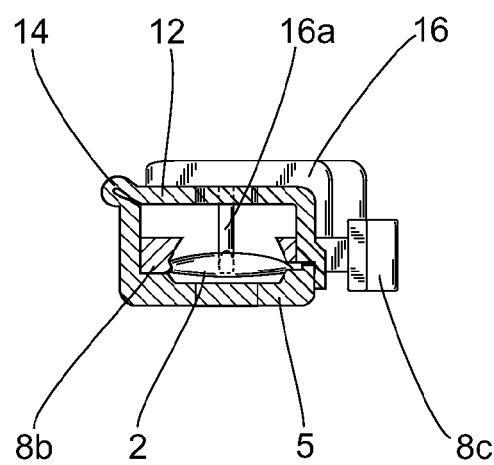
FIG. 6 is a cross-section view from the B-B direction of FIG. 5.

FIG. 6 is a cross-section view showing FIG. 5 from the B-B direction and shows the state of the lens 2 set in the lens placing section 5. When the lens 2 is set in the lens placing section 5, operating the operation member 8c of the folding members 8 moves the compression member 8b to the outward position to obtain a space in which the optical area 2a can be placed in the lens placing section 5. Of course, when setting the lens 2, the protective cover 16 must be removed and the open/close lid 12 opened. The movement of the set lens 2 is restricted by the protrusions 16a provided in the protective cover 16.

Figure 7:
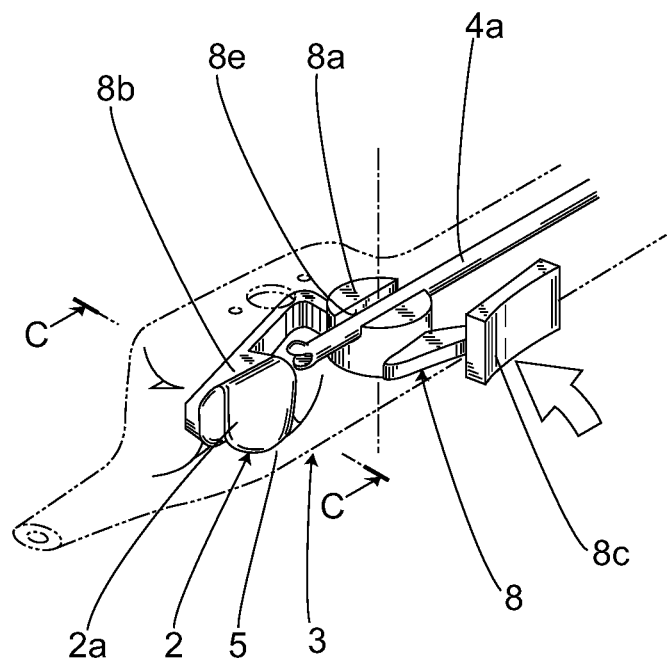
FIG. 7 is an oblique perspective view showing the lens in the folded state according to the second embodiment of the present invention.

FIG. 7 is a drawing that corresponds to FIG. 5 and shows the state of the lens 2 being folded when the operation of the operation member 8c of the folding members 8 is moved to the body 3 side. When folding the lens 2, first remove the protective cover 16 from the body 3. When this is done, the press holder 11b that restricted the movement of the operation member 8c of the folding members 8 is removed together with the protective cover 16 to make the folding operation of the lens 2 possible. Here, pushing the operation member 8c of the folding members 8 to the side of the body 3 will rotate the folding members 8 centering on the boss 8a causing the compression member 8b to compress an edge of the optical area 2a of the lens 2. If an edge of the optical area 2a of the lens 2 is compressed, the lens 2 will be caught between the inner wall of the body 3 and the compression member 8b and folded by the resulting compression. Then, when the boss 8a of the folding members 8 rotates, the direction of the through groove 8e provided in the boss 8a and the direction of the plunger shaft 4a will align. In this manner, after the lens 2 is folded, the optical area 2a of the folded lens 2 is pressed and moved by the operation of the plunger 4. Therefore, when using the plunger 4 to implant the lens 2 in an eye, the plunger 4 presses on the optical area 2a of the lens 2 to implant the lens 2.

Figure 8:
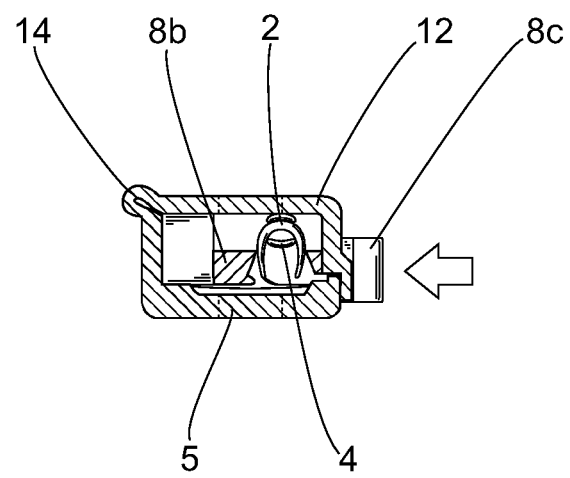
FIG. 8 is a cross-section view showing the lens in the folded state taken on the C-C line of FIG. 7.

FIG. 8 shows a cross-section view of FIG. 7 from the C-C direction, which shows the state of the lens 2 after folding. When using the injector 1 to implant the intraocular lens 2, the outer edge of the optical area 2a is pressed and implanted by the plunger 4 after the lens 2 is folded as shown in FIG. 8. On the other hand, when using tweezers 15 to grasp the lens 2 and implant it without using the injector 1, the folded lens 2 shown in FIG. 8 is grasped by the tweezers 15 by opening the open/close lid 12 and then the folded lens 2 is implanted in the eye (see, e.g., FIG. 15).

Figure 9:
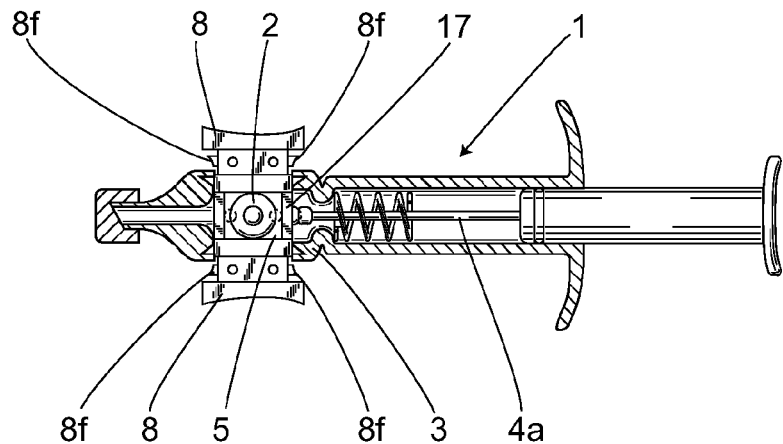
FIG. 9 is a cross-section view of the intraocular lens inserting instrument of a third embodiment of the present invention.

FIG. 9 to FIG. 12 show an intraocular lens inserting instrument 1 according to the third embodiment of the present invention, and FIG. 9 is a drawing showing the state with the protective cover 16 removed. The construction of the folding members 8 and the open/close lid 12 of this embodiment differs from the afore-mentioned first embodiment and second embodiment, with the remaining construction being had in common. Therefore, the explanation of the areas in common with the first embodiment and the second embodiment is omitted and the folding members 8 and open/close lid 12 having a differing construction are explained.

This embodiment comprises two folding members 8 such that both sides of the optical area 2a of the lens 2 are caught between the folding members 8 and folded. Further, the two folding members 8 are positioned in a location axially symmetric to the lens placing section 5 and are joined by a plate spring 17. In addition, the embodiment has a construction wherein the folding members 8 are provided with protrusions 8f in suitable locations where the protrusions 8f latch into depressions or the like provided in the body 3. This injector 1 having this construction is maintained in the state where the folding members 8 are pulled outward to prevent the plate spring 17 from compressing the lens 2 when it is set in the lens placing section 5. This state obtains space for storing the lens 2 between the two folding members 8 and 8.

Figure 10:
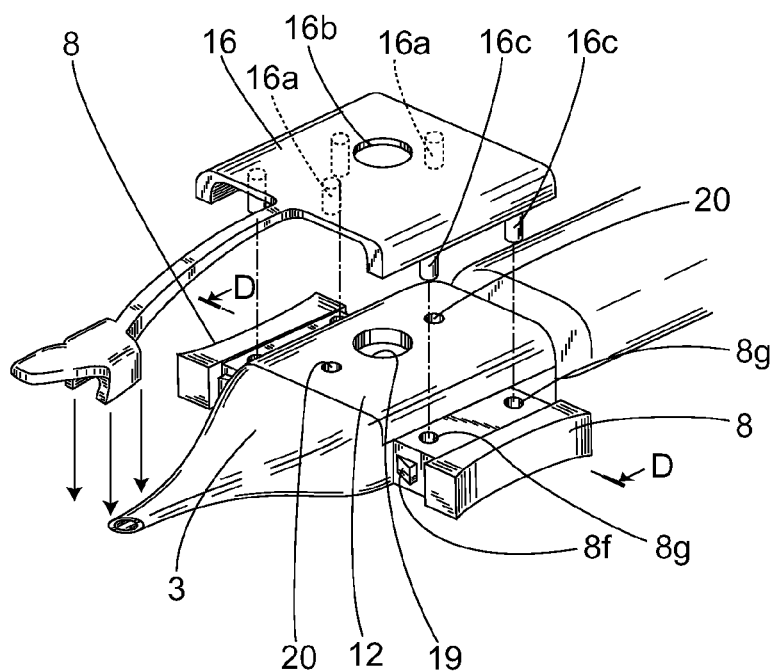
FIG. 10 is an oblique perspective view showing the third embodiment including a removable protective cover.

After setting the lens 2, the protective cover 16 is mounted on the body 3 as shown in FIG. 10. In this manner the position of the lens 2 is fixed and the movement of the two folding members 8 and 8 is restricted by the locking mechanisms 8g and 16c. In other words, the back of the protective cover 16 is provided with protrusions 16a in two locations for fixing the position of the lens 2 and protrusions 16c provided in four locations for fixing the movement of the folding members 8, and the mounting of the protective cover 16 on the body 3 locks the movement of the lens 2 and the folding members 8. More specifically, the protrusions 16a provided in two locations on the back of the protective cover 16 are inserted into the two holes 20 provided in the open/close lid 12 to restrict the movement of the optical area 2a of the lens 2. Further, the protrusions 16c of the protective cover 16 are inserted into the locking holes 8g provided in the folding members 8 to lock the folding members 8.

The open/close lid 12 shown in FIG. 10 has a construction separate from the body 3, but a hinge or other device can be used to make it an integrated structure with the body 3.

Figure 11A:
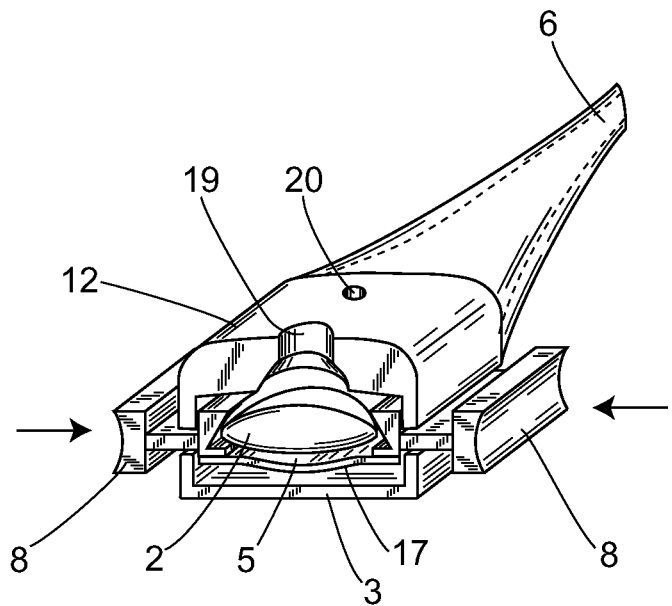
Figure 11B:
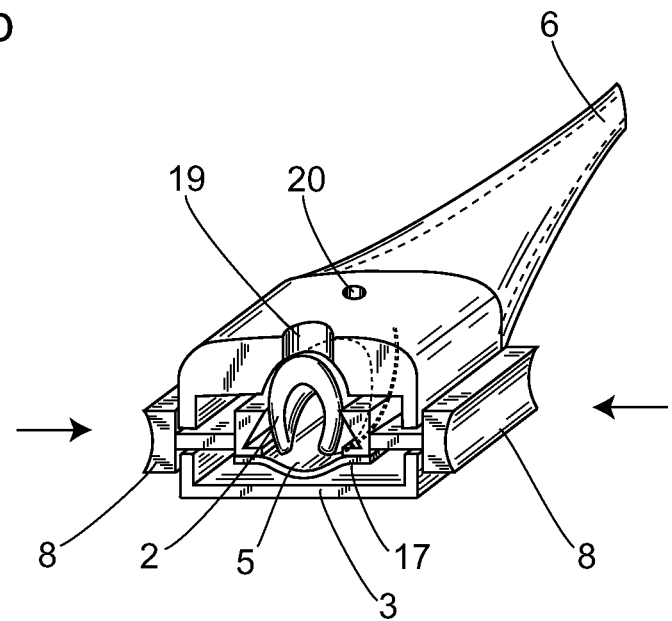

FIG. 11 is an oblique perspective view showing the structure as viewed from the D-D direction of FIG. 10 where (a) shows the preset state and (b) shows the state after the lens is folded. The preset state shown in (a) is positioned such that stress is not applied to the optical area 2a of the lens 2. In the folded state shown in (b), the optical area 2a of the lens 2 is pressed from both sides to fold it into a shape with a U-shape. Here, the open/close lid 12 mounted on top of the lens placing section 5 is provided with an inspection hole 19 through which the state of the lens 2 can be viewed and a through hole 20 through which the protrusion 16a of the protective cover 16 is inserted.

Figure 12A:
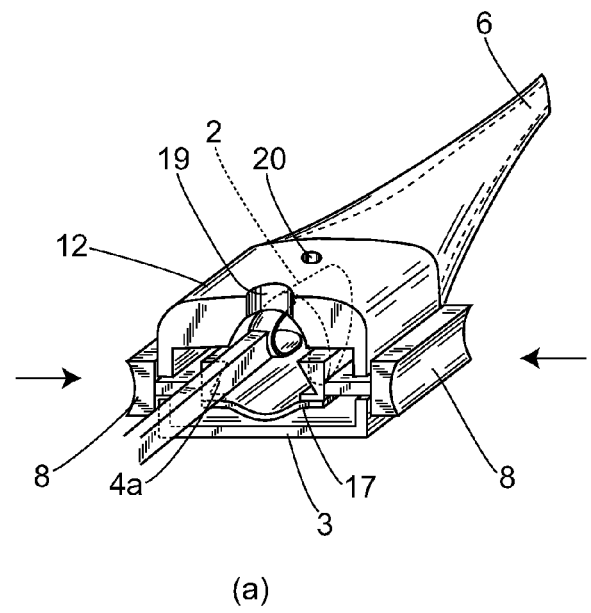
Figure 12B:
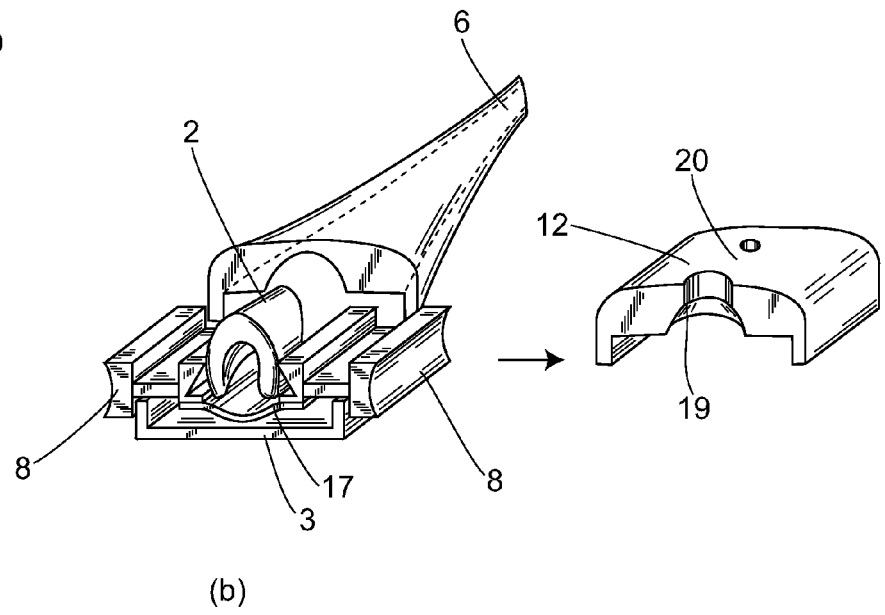

FIG. 12 is a drawing showing the same part as FIG. 11 and is for explaining the implanting method of the lens 2 after the lens is folded. More specifically, it is an oblique perspective view of FIG. 10 from the D-D direction where (a) shows the case of the lens 2 being discharged by the plunger shaft 4a and (b) shows the case of the lens 2 being grasped by the tweezers 15. When using the injector 1 to implant the lens 2, the lens 2 is pushed from both sides and folded by both folding members 8 as shown in (a) and then the lens 2 is discharged and implanted by the plunger shaft 4a. On the other hand, when the injector 1 is not used and the lens 2 is grasped and implanted by the tweezers 15, the open/close lid 12 is removed after the lens is folded and then the tweezers 15 may be used to grasp the folded lens 2 and implant it in the eye as shown in (b) (see, e.g., FIG. 15).

Figure 13:
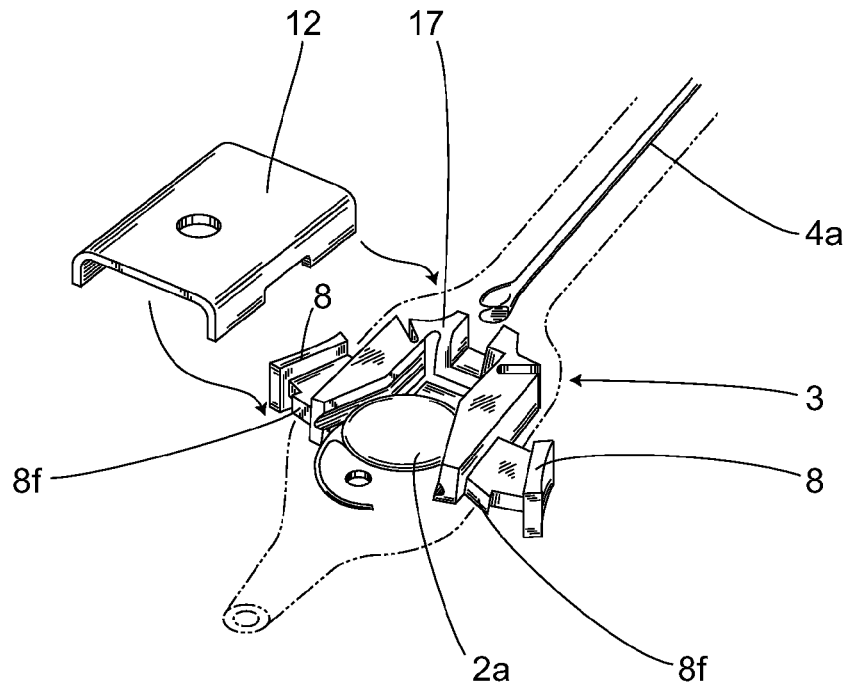
FIG. 13 shows an oblique perspective view of the intraocular lens inserting instrument of a fourth embodiment of the present invention.
Figure 14:
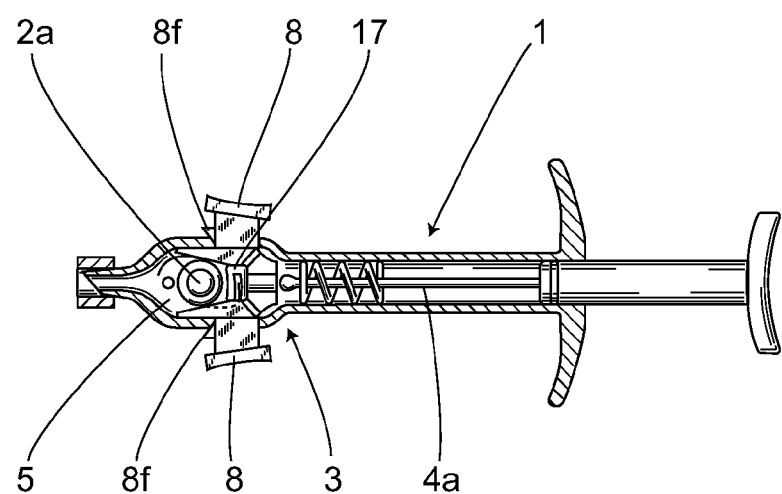
FIG. 14 shows a cross-section view of the intraocular lens inserting instrument of the fourth embodiment of the present invention.

FIG. 13 and FIG. 14 show an intraocular lens insertion instrument 1 according to the fourth embodiment of the present invention, and show the state with the open/close lid 12 removed. Although this embodiment has the same construction as the afore-mentioned third embodiment, the detailed construction of the folding members 8 differs from that of the third embodiment. Therefore, the explanation of the areas in common with the third embodiment is omitted and the folding members 8 having a construction that differs from that of the third embodiment are explained.

This embodiment provides two folding members 8 in the lens placing section 5 where the afore-mentioned two folding members 8 are joined by a plate spring 17 and protrusions 8f are provided in the afore-mentioned two folding members 8 that lock at appropriate locations in the body 3 to counter the bias force of the afore-mentioned plate spring 17 to maintain the position of the afore-mentioned folding members 8. However, the joining method using the plate spring 17 differs from that of the third embodiment. The two folding members 8 are positioned in a V-shape with one edge connected to the plate spring 17. Further, the two folding members 8 are made to only rotate at a specific angle about the center of the plate spring 17. In other words, when the two folding members 8 are opened outwards, the two folding members 8 are positioned in a V-shape in the lens placing section 5 to obtain space for placing the optical area 2a of the lens. Therefore, this state allows for the lens 2 to be positioned without excess stress being placed on the optical area 2a of the lens. After the lens is positioned, the open/close lid 12 is mounted on the body 3 to complete the setting of the lens 2. In addition, although not shown in the figure, the back of the open/close lid 12 is provided with a multiplicity of protrusions to fix the position of the lens 2 and a multiplicity of protrusions to fix the movement of the folding members 8 such that when the open/close lid 12 is mounted on the body 3, the movement of the lens 2 and the movement of the folding members 8 are restricted. Further, the open/close lid 12 is provided with an abutment that restricts the movement of the plunger shaft 4a to prevent the lens 2 from being discharged by mistaken operation of the plunger 4.

Figure 15:
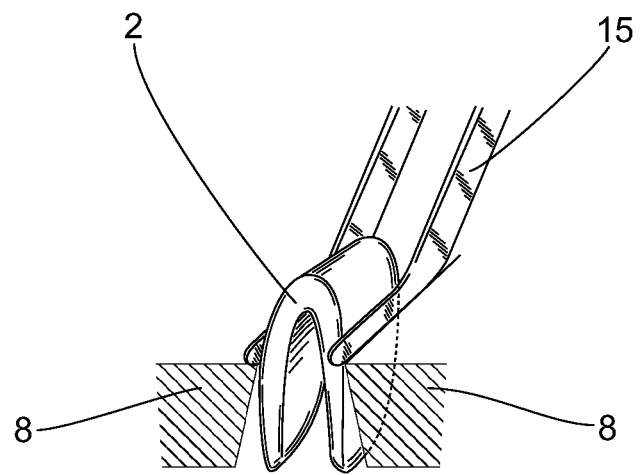
FIG. 15 shows a folded lens being grasped by tweezers according to principles of the present invention.

FIG. 15 shows tweezers 15 being used to grasp the lens 2 without using the injector 1. After the lens 2 has been folded, the fold of the lens 2 protrudes above the folding members 8 to allow the lens 2 to be easily grasped by the tweezers 15.

An explanation of the present invention based on several embodiments was given above, but this explanation in no way intended to restrict the scope of the invention over the scope as defined by plain meaning of the claims. For example, in the above embodiments the case where the method of joining two folding members 8 with a separate plate spring 17 was shown, but the two folding members and spring material could for example be alternatively formed as a single piece.

The invention claimed is:

1. A preset intraocular lens inserting instrument, comprising:
   a tubular body that defines a longitudinal axis and includes a main portion on the longitudinal axis, a nozzle on the longitudinal axis that is configured to be inserted into the eye, and a lens placing section located on the longitudinal axis between the main portion and the nozzle;
   an unfolded intraocular lens located within the lens placing section such that at least a portion of the unfolded intraocular lens is on the longitudinal axis;
   a folding member, movable relative to the lens placing section between a first position and a second position, that folds the unfolded intraocular lens while moving from the first position to the second position; and
   a plunger on the longitudinal axis and movable through the tubular body to push the folded intraocular lens into the eye;
   wherein the plunger and the folding member are operably associated with one another such that the plunger is prevented from moving into contact with the unfolded intraocular lens within the lens placing section when the folding member is in the first position and the plunger is not prevented from moving into contact with the folded intraocular lens when the folding member is in the second position.

2. An intraocular lens inserting instrument according to claim 1, wherein the folding member the intraocular lens in two.

3. An intraocular lens inserting instrument according to claim 1, wherein the lens placing section includes a lid.

4. An intraocular lens inserting instrument according to claim 3, wherein the lid is attached to the tubular body by a hinge.

5. An intraocular lens inserting instrument according to claim 1, wherein the folding member is configured such that tweezers may be used to grasp and remove the intraocular lens from the lens placing section.

6. An intraocular lens inserting instrument according to claim 1, wherein the folding member comprises first and second folding elements that are joined by a plate spring and are provided with a protrusion that opposes the bias force of the plate spring to maintain the position of the folding elements.

7. An intraocular lens inserting instrument according to claim 1, further comprising:
   a locking mechanism associated with the folding member that prevents the folding member from folding the intraocular lens when in a locked state.

8. An intraocular lens inserting instrument according to claim 3, wherein the lid includes an inspection hole.

9. An intraocular lens inserting instrument according to claim 3, wherein the folding member is locked when the lid is in a closed position.

10. An intraocular lens inserting instrument according to claim 1, wherein the folding member is movable in a direction perpendicular to the longitudinal axis.

11. An intraocular lens inserting instrument according to claim 1, wherein
    the folding member includes a boss, rotatably mounted in the lens placing section, that includes a compression member and an operation member that extends outward from the lens placing section.

12. A preset intraocular lens inserting instrument that inserts a folded intraocular lens into an eye, comprising:
- a tubular body defining a longitudinal axis along which said intraocular lens is guided to the eye;
- a plunger movable along said longitudinal axis that presses and discharges said intraocular lens into the eye;
- a lens placing section located along said longitudinal axis in said tubular body to contain said intraocular lens in an unfolded state; and
- a folding member, which is movable relative to the lens placing section, that folds said intraocular lens in said lens placing section by moving from a first position where said intraocular lens is unfolded to a second position where said intraocular lens is folded;
- wherein said folding member prevents said plunger from contacting said intraocular lens before the folding of said intraocular lens and permits said plunger to contact said intraocular lens after the folding of said intraocular lens.

13. An intraocular lens inserting instrument according to claim 1, wherein a portion of the folding member prevents the plunger from moving into contact with the intraocular lens when the folding member is in the first position.

14. An intraocular lens inserting instrument according to claim 1, wherein a portion of the folding member abuts the plunger when the folding member is in the first position.

15. A preset intraocular lens inserting instrument as claimed in claim 12, wherein the lens placing section is not movable relative to the tubular body.

* * * * *